US008633267B2

(12) United States Patent
Gelbin et al.

(10) Patent No.: US 8,633,267 B2
(45) Date of Patent: *Jan. 21, 2014

(54) LIQUID PHOSPHITE COMPOSITIONS HAVING DIFFERENT ALKYL GROUPS

(75) Inventors: Michael E. Gelbin, Middlebury, CT (US); Jonathan S. Hill, Flixton (GB); Maurice Power, Old Trafford (GB)

(73) Assignee: Addivant USA LLC, Middlebury, CT (US)

( * ) Notice: Subject to any disclaimer, the term of this patent is extended or adjusted under 35 U.S.C. 154(b) by 520 days.

This patent is subject to a terminal disclaimer.

(21) Appl. No.: 12/804,680

(22) Filed: Jul. 26, 2010

(65) Prior Publication Data

US 2011/0028616 A1 Feb. 3, 2011

Related U.S. Application Data

(60) Provisional application No. 61/230,652, filed on Jul. 31, 2009.

(51) Int. Cl.
*C08G 18/77* (2006.01)
*C08K 5/49* (2006.01)
*C08K 5/51* (2006.01)
*C08K 5/00* (2006.01)
*C08C 19/02* (2006.01)

(52) U.S. Cl.
USPC .................. 524/151; 524/115; 524/147

(58) Field of Classification Search
USPC .......................................... 524/115, 147, 151
See application file for complete search history.

(56) References Cited

U.S. PATENT DOCUMENTS

| 3,056,823 | A | 10/1962 | Hechenbleikner et al. |
| 3,533,989 | A | 10/1970 | Westcott, Jr. |
| 5,254,709 | A | 10/1993 | Hunter |
| 7,468,410 | B2 | 12/2008 | Chafin et al. |
| 7,888,414 | B2 * | 2/2011 | Gelbin et al. ................. 524/128 |
| 8,178,005 | B2 * | 5/2012 | Gelbin et al. ............ 252/400.24 |
| 8,183,311 | B2 * | 5/2012 | Gelbin et al. ................. 524/128 |
| 8,188,170 | B2 * | 5/2012 | Zahalka et al. ............... 524/101 |
| 2007/0021537 | A1 | 1/2007 | Chafin et al. |
| 2010/0004363 | A1 | 1/2010 | Gelbin et al. |
| 2010/0025636 | A1 | 2/2010 | Gelbin et al. |

FOREIGN PATENT DOCUMENTS

| CA | 2464551 | 11/2005 |
| JP | 59-30842 | 2/1984 |
| WO | WO 93/03092 | 2/1993 |
| WO | WO-2006/066947 A1 | 6/2006 |
| WO | WO-2007/149143 A2 | 12/2007 |

* cited by examiner

*Primary Examiner* — Angela C Scott
(74) *Attorney, Agent, or Firm* — D'Hue Law LLC; Cedric D'Hue

(57) ABSTRACT

A composition comprising a mixture of at least two different alkylaryl phosphites, wherein some alkyl groups have a different number of carbon atoms than other alkyl groups and wherein the mixture is a liquid at ambient conditions.

18 Claims, No Drawings

LIQUID PHOSPHITE COMPOSITIONS HAVING DIFFERENT ALKYL GROUPS

This application claims benefit under 35 USC 119(e) of U.S. provisional application No. 61/230,652, filed Jul. 31, 2009, the disclosure of which is incorporated by reference.

FIELD OF THE INVENTION

The present invention relates to novel phosphite compositions suitable for use as antioxidants in polymer compositions. It also relates to stabilized polymer compositions and stabilizer concentrates comprising the novel liquid phosphite compositions.

BACKGROUND OF THE INVENTION

Organic phosphites are well-known and are commonly used as secondary antioxidants in polymer compositions including, for example, polyolefins, polyvinyl chloride, and elastomers. Examples of such phosphites are disclosed in H. Zweifel (Ed) *Plastics Additives Handbook*, 5th edition, Hanser Publishers, Munich 2000. Phosphite stabilizers, both liquid and solid, are known in the art.

Solid organic phosphite stabilizers are widely used as secondary antioxidants in polymer compositions. One commercially available antioxidant is tris(2,4-di-t-butylphenyl) phosphite, shown below, a solid antioxidant commonly known as Alkanox™ 240, Irgafos™ 168 and Doverphos™ S-480. U.S. Pat. No. 5,254,709, the entirety of which is incorporated herein by reference, describes the synthesis of tris(2,4-di-t-butylphenyl)phosphite by reacting 2,4-di-t-butyl phenol with phosphorus trichloride in the presence of catalyst. The isolated phosphite is described as a white crystalline solid having a melting between 180-185° C.

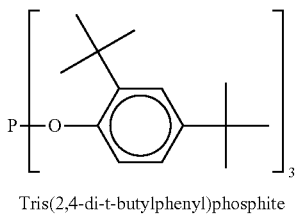

Tris(2,4-di-t-butylphenyl)phosphite

Tris(2,4-di-t-butylphenyl)phosphite has been demonstrated to effectively reduce peroxide induced oxidative degradation for many polymers including polyolefins, polycarbonates, ABS and polyesters. The trialkylaryl phosphite has low volatility that allows for its use at high temperatures commonly required for processing thermoplastic polymers. Owing to its solid form and concomitant processing limitations, however, tris(2,4-di-t-butylphenyl)phosphite is not well-suited for the stabilization of all polymers and has been demonstrated to plate out during processing of some plastics, in particular low melting point plastics, and forming deposits on processing machinery surfaces.

Liquid phosphite compositions are also well known and do not possess the handling problems associated with solid phosphite compounds. In addition, liquid phosphite compositions generally exhibit better processability than solid phosphite compositions for polymers that process at low temperatures. Tris(p-nonylphenyl)phosphite (TNPP), for example, is one alkylaryl phosphite that is a stable liquid at ambient conditions.

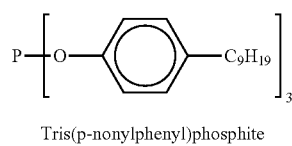

Tris(p-nonylphenyl)phosphite

TNPP is a versatile phosphite stabilizer that is useful in stabilizing a large number of polymers such as HDPE, LLDPE, SBR, ABS, PVC and others. There is, however, a need to replace TNPP due to the alleged estrogenicity of nonylphenol, which is commonly used in the synthesis of TNPP.

Many commercially available alkylaryl phosphites share a common alkyl group. U.S. Pat. No. 5,254,709, for example, the entirety of which is incorporated herein by reference, describes the synthesis of tris(2,4-di-t-butylphenyl)phosphite by reacting a 2,4-di-t-butyl phenol with phosphorus trichloride in the presence of catalyst according to the following reaction:

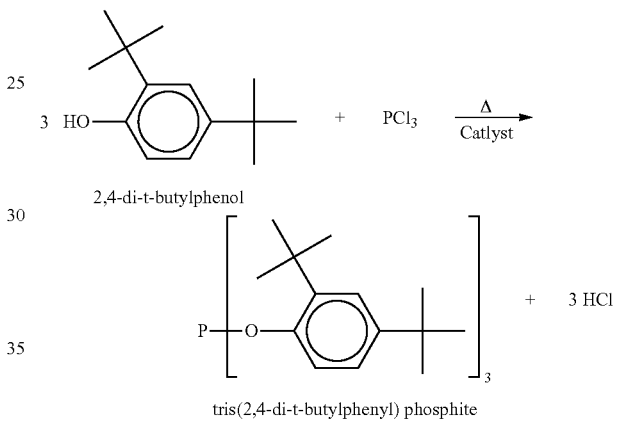

U.S. Pat. No. 7,468,410 describes a mixture of phosphites including a tri(4-sec-butylphenyl)phosphite and a tri(2-sec-butylphenyl)phosphite. Each of these phosphites is a liquid when isolated, and the combination is a liquid.

U.S. Pat. No. 5,254,709 describes various secondary antioxidants including a solid phosphite made from 2:1 molar ratio of 2,4-di-t-amyl phenol and 2,4-di-t-butyl phenol, and a liquid phosphite made from 2-t-butyl-4-nonyl phenol.

The need remains for novel, safe and effective phosphite stabilizers that can effectively stabilize polymer resins and compositions against heat and light degradation and that are liquid at ambient conditions.

SUMMARY OF THE INVENTION

The invention is directed to various compositions comprising a mixture of at least two different alkylaryl phosphites, wherein some alkyl groups have a different number of carbon atoms than other alkyl groups and wherein the mixture is a liquid at ambient conditions. The first and second phosphites broadly correspond to the structure:

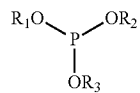

wherein $R_1$, $R_2$, and $R_3$ are independently selected alkylated aryl groups, each aryl moiety being an independently selected aromatic moiety of from 6 to 18 carbon atoms, and wherein each aromatic moiety is substituted with at least one straight or branched $C_1$-$C_{18}$ alkyl group. Typically $R_1$, $R_2$, and $R_3$ are independently selected alkylated aryl groups of the structure:

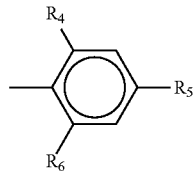

wherein $R_4$, $R_5$, and $R_6$ are independently selected from the group consisting of hydrogen and straight or branched $C_1$-$C_8$ alkyl provided that at least one of $R_4$, $R_5$, and $R_6$ is not hydrogen.

Thus, at least the first and second alkylaryl phosphites of the inventive composition, while different, each have the general structure:

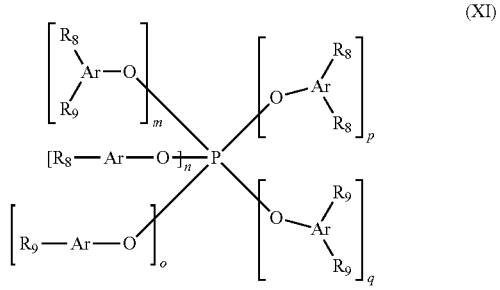
(XI)

wherein m, n, o, p and q are integers independently selected from 0, 1, 2 and 3 provided that m+n+o+p+q=3, each Ar is an independently selected aromatic moiety of 6 to 18 carbon atoms, typically phenyl, each $R_8$ is a straight or branched $C_1$-$C_{18}$ alkyl group having the same number of carbon atoms and each $R_9$ is a straight or branched $C_1$-$C_{18}$ alkyl group having the same number of carbon atoms, provided that $R_8$ has a different number of carbon atoms than $R_9$ and the first phosphite contains an aromatic moiety substituted by at least one $R_8$ and the second phosphite contains an aromatic moiety substituted by at least one $R_9$. $R_8$ and $R_9$ are independently selected from straight or branched $C_1$-$C_{18}$ alkyl groups, for example, straight or branched $C_1$-$C_{12}$ alkyl groups, such as isomers of propyl, butyl and amyl, for example, isopropyl, sec-butyl, t-butyl, sec-amyl and t-amyl. Where the aromatic moiety is phenyl, each respective alkyl group is typically in the ortho and/or para positions, although other positions are possible.

In a first general embodiment, the phosphite composition comprises a first alkylaryl phosphite having the structure:

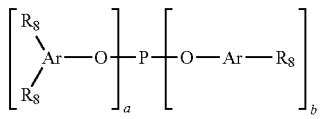

and a second alkylaryl phosphite having the structure:

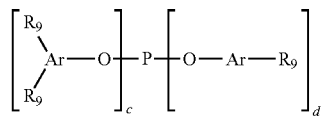

wherein a, b, c, and d are independently integers selected from 0, 1, 2, and 3, provided that a+b=3 and c+d=3, and Ar, $R_8$ and $R_9$ are as defined above.

In a second general embodiment, the phosphite composition comprises one or more phosphites having the structure:

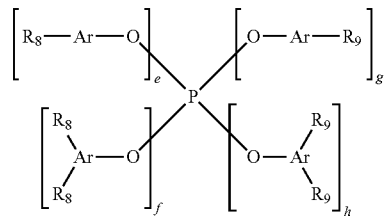

wherein e, f, g and h are independently selected from 0, 1 and 2, provided that e+f+g+h=3, e+f=1 or 2, and g+h=1 or 2, and Ar, $R_8$ and $R_9$ are as defined above.

In a third general embodiment, the phosphite composition comprises one or more phosphites of the structure XI wherein m is an integer selected from 1, 2 and 3; n, o, p and q are integers independently selected from 0, 1 and 2, provided that m+n+o+p+q=3, and Ar, $R_8$ and $R_9$ are as defined above. In this embodiment, the phosphite composition comprises at least two different alkylaryl phosphites, wherein at least one of the alkylaryl phosphites has at least one aryl moiety with two or more alkyl groups having a different number of carbon atoms.

In another embodiment, the invention is to a composition comprising a mixture of at least two different alkylaryl phosphites, wherein at least one of the alkylaryl phosphites has two or more alkyl groups having a different number of carbon atoms which alkyl groups are substituents on different aryl moieties, and wherein the mixture is a liquid at ambient conditions.

The phosphite composition is conveniently prepared by reacting a phosphorous trihalide, for example, $PCl_3$, with a mixture of at least two different alkylaryl phosphites.

DETAILED DESCRIPTION OF THE INVENTION

The present invention provides phosphite compositions, which are liquid at ambient conditions, comprising at least two different alkylaryl phosphites provided that the phosphite composition includes two or more alkyl groups, whether on the same or different phosphite compounds, wherein the two or more alkyl groups having a different number of carbon atoms. The incorporation of the two or more alkyl groups having a different number of carbon atoms are leads to at least three different general embodiments of the present invention as follows:

(i) Mixed Phosphite Embodiment. In the first general embodiment, the two or more alkyl groups having a different number of carbon atoms are on different phosphite compounds. That is, at least one phosphite bears aryl groups substituted with alkyl groups having a first number of carbon atoms and another phosphite bears aryl groups substituted with alkyl groups having a second number of carbon atoms, where the first and second numbers are different. The first embodiment is referred to as the "mixed phosphites" embodiment as such compositions are conveniently formed by mixing two separately synthesized phosphites or phosphite mixtures.

(ii) Mixed Alkylate Embodiment. In the second general embodiment, the two or more alkyl groups having a different number of carbon atoms can be found on adjacent aryl moieties of a single phosphite compound. That is, a phosphite of this embodiment comprises one or more aryl moieties substituted with an alkyl group having the first number of carbon atoms and also one or more aryl moieties substituted with an alkyl group having a second number of carbon atoms, where the first and second numbers are different. The second embodiment is referred to as "mixed alkylates" embodiment because such phosphite compositions are conveniently formed by reacting a phosphorous halide with an alkylate composition comprising at least two separately synthesized alkylates or alkylate mixtures.

(iii) Mixed Olefins Embodiment. In a third general embodiment, the two or more alkyl groups having a different number of carbon atoms may both be on the same aryl moiety of one or more phosphites. The third embodiment is referred to as "mixed olefins" embodiment because such compositions are conveniently formed by reacting a mixture of olefins having a different number of carbon atoms with a hydroxyaryl compound to form a complex alkylate composition, and reacting this alkylate composition with a phosphorous halide.

It should be appreciated that two or more of the first, second and third embodiments may be combined to form even more diverse phosphite compositions.

While the various embodiments of the present invention lead to different phosphite compositions, there are certain characteristics shared by each phosphite composition. The phosphite compositions are liquid at ambient conditions. By "ambient conditions" it is meant room temperature, e.g., 25° C., and 1 atmosphere pressure. As discussed herein, the fact that the phosphite compositions are liquid at ambient conditions is surprising and unexpected because in most cases it would be expected that each of the individual phosphites contained in the phosphite composition, when isolated, would be a solid at ambient conditions. This is particularly surprising given that the prior art teaches several examples of solid phosphite compositions, the components of which are separately solids at ambient condition, (See JP 59030842; WO 9303092; CA 2,464,551; U.S. Pat. No. 5,254,709). In contrast, phosphite compositions of the invention are liquid even though the individual components would be expected to be solid.

Table 1 provides the melting points, each of which is above room temperature, for several pure phosphite compounds.

TABLE 1

| Phosphite | Melting Point |
|---|---|
| tris(4-t-butylphenyl) phosphite | 75-76° C. |
| tris(2,4-di-tertbutylphenyl) phosphite | 181-184° C. |
| bis(4-t-butylphenyl)-2,4-di-t-butylphenyl phosphite | 63-65° C. |
| bis (2,4-di-t-butylphenyl)-4-t-butylphenyl phosphite | 100-103° C. |
| tris(4-t-amylphenyl) phosphite | 52-54° C. |
| tris(2,4-di-t-amylphenyl) phosphite | 103° C. |

As used herein, by "liquid," it is meant that the phosphite composition remains liquid after at least three "freeze/thaw" cycles as opposed to "meta-stable liquids," which do not remain liquid after three or fewer cycles. A freeze/thaw cycle is defined as follows: 1) An ambient temperature composition is stirred for 0.5 hours; 2) The stirred composition is then refrigerated at about −5 to −10° C. for three days; and 3) The refrigerated composition is then brought to ambient temperature, and held at ambient for 3 days. After step 3, the composition is checked for solids content, e.g., crystallization. Completion of steps 1-3 defines one freeze/thaw cycle.

The viscosity of the phosphite composition will vary depending on the relative amounts of the various phosphite compounds contained therein. In some exemplary embodiments, the phosphite composition has a viscosity less than 11,000 cSt, e.g., less than 7,300 cSt, less than 5,000 cSt, less than 3,000 cSt, or less than 2850 cSt, these viscosities being measured at 30° C. Thus, the viscosity of the composition may range from 1 cSt to 15,000 cSt, from 100 cSt to 12,000 cSt, from 500 cSt to 10,000 cSt, from 500 cSt to 6,500 cSt, from 500 cSt to 5,000 cSt, from 500 cSt to 3,000 cSt, from 1,000 cSt to 4,000 cSt, from 1,500 cSt to 3,500 cSt, from 2,000 cSt to 3,000 cSt, or from 2,000 to 2,800 cSt, these viscosities being measured at 30° C.

It has now been discovered that by increasing the diversity of the alkylaryl phosphites in the phosphite composition, handling characteristics (e.g., liquid physical state and viscosity) as well as solubility/compatibility with various polymers can be advantageously improved. The invention provides various ways to increase phosphite diversity by incorporating alkyl groups having different numbers of carbon atoms. In various embodiments, for example, the liquid composition may comprise at least 2, e.g., at least 4 or at least 10, different alkylaryl phosphites, and optionally from 2 to 100 different alkylaryl phosphites, e.g., from 3 to 20 different alkylaryl phosphites or from 4 to 10 different alkylaryl phosphites.

Another advantage of the present invention is that alkylaryl phosphites derived from mixed alkylates helps to mitigate processing costs and eliminates the conventional need for substantially pure starting materials (e.g., olefins and/or alkylated phenolics).

Generally, each phosphite in the composition has the structure:

(I)

wherein $R_1$, $R_2$, and $R_3$ are independently selected alkylaryl groups and wherein the composition is a liquid at ambient conditions.

The aryl moiety (Ar) present in the compounds of the present invention is an aromatic moiety of from 6 to 18 carbon atoms, e.g., phenyl, naphthyl, phenanthryl, anthracyl, biphenyl, terphenyl, o-cresyl, m-cresyl, p-cresyl, xylenols and the like, preferably phenyl.

Generally, each aromatic moiety is substituted with at least one branched or straight chain $C_1$-$C_{18}$ alkyl group, e.g., $C_1$-$C_{12}$ alkyl group, $C_2$-$C_6$ alkyl group or $C_3$-$C_5$ alkyl group, but in certain embodiments a minor amount of phosphites bearing an unsubstituted aromatic moiety is present. In one embodiment, the two or more alkyl groups having a different number of carbon atoms are selected from branched or straight chain $C_1$-$C_{12}$ alkyl group, e.g., a $C_3$-$C_5$ alkyl group, or $C_4$-$C_5$ alkyl group. The alkyl groups are selected, for example, from the group consisting of methyl, ethyl, propyl, butyl, amyl, hexyl, heptyl, octyl, decyl, undecyl, dodecyl, tridecyl, tetradecyl, pentadecyl, hexadecyl, heptadecyl, octadecyl, and isomers thereof; the alkyl group may be nonyl, but this is generally avoided. In particular embodiments the alkyl groups are selected from propyl, butyl and amyl groups, for example, isopropyl, sec-butyl, t-butyl, sec-amyl, t-amyl and neo-amyl. In many embodiments, neither of the alkyl groups is $C_8$-$C_{10}$ alkyl, e.g., $C_9$ alkyl. Thus, in a preferred embodiment, the alkyl moieties do not include nonyl, meaning the phosphite composition preferably comprises less than 50 wppm, e.g., less than 10 wppm or less than 5 wppm nonyl substituted aryl phosphite compounds, and most preferably no detectable nonyl substituted aryl phosphite compounds. In addition, the phosphite composition preferably comprises less than 50 wppm, e.g., less than 10 wppm or less than 5 wppm nonylphenol, and most preferably no detectable nonylphenol.

The aromatic moieties are mono, di and to a lesser extent, tri substituted, generally in the ortho and/or para positions, but each phosphite of the composition does not contain exclusively mono substituted aryls or exclusively disubstituted aryls or exclusively trisubstituted aryls. Typically, the phosphite compositions of the invention generally include some phosphite compounds having aryl moieties that are monoalkylated and dialkylated. The combination of mono and di-substituted aryl moieties in combination with employing different alkyl groups allows for very diverse phosphite compositions. A small amount, if any of the aryl moieties are trisubstituted, for example either 0 to 5 wt % or 0.1 to 5 wt % of the aryl moieties are trisubstituted, for example, 1-3 wt %, e.g. 2-3 wt % are trisubstituted. Often fewer than 3 wt % of the aryl moieties are trisubstituted, e.g., fewer than 2 wt %, or fewer than 1 wt %.

Typically, few if any of the aryl moieties are monosubstituted in the ortho position, for example 0 to 5 wt % and often less than 3 wt %, e.g., less than 2 wt % or less than 1 wt % of the aryl moieties are monosubstituted in the ortho position. In some embodiments, for example 0.1 to 5 wt %, 1-3 wt %, or 2-3 wt % of the aryl moieties are monosubstituted in the ortho position. There may also be a similarly small amount of unsubstituted aryl groups.

The phosphite composition may contain phosphite compounds having aryl groups that are substituted with alkyl groups having hydrogen atoms in the a position, for example, n-propyl, iso-propyl, n-butyl, iso-butyl, sec-butyl, n-amyl, sec-amyl, iso-amyl and the like. In other embodiments, the phosphite composition is substantially free of phosphite compounds having aryl groups that are substituted with alkyl groups having hydrogen atoms in the a position, for example, in some embodiments, at least 95%, at least 98% or at least 99% of the aryl moieties are substituted with alkyl groups having tertiary α-carbons, for example, t-butyl and/or t-amyl.

$R_1$, $R_2$, and $R_3$ are, for example, independently selected alkylated aryl groups of the structure:

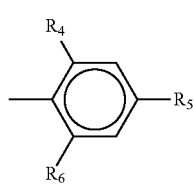

(II)

wherein $R_4$, $R_5$, and $R_6$ are independently selected from the group consisting of hydrogen and straight or branched $C_1$-$C_8$ alkyl, e.g., methyl, ethyl, propyl, butyl, amyl, hexyl, heptyl, octyl, and isomers thereof, e.g., isopropyl, sec-butyl, t-butyl, sec-amyl, t-amyl, neo-amyl, provided that at least one of $R_4$, $R_5$, and $R_6$ is not hydrogen. In one embodiment $R_4$ and $R_6$ are hydrogen, and $R_5$ is not hydrogen. In one embodiment, the ortho alkyl groups, i.e., $R_4$ and $R_6$, have no α-hydrogen atoms. In one embodiment, the ortho alkyl groups, i.e., $R_4$ and $R_6$, have tertiary α-carbon atoms selected from the group consisting of t-butyl and t-amyl.

In one embodiment, $R_4$ and $R_5$ are independently selected from the group consisting of methyl, ethyl, propyl, butyl, amyl, hexyl, and isomers thereof, and $R_6$ is hydrogen. In another embodiment, $R_4$ and $R_6$ are hydrogen and $R_5$ is independently selected from the group consisting of methyl, ethyl, propyl, butyl, amyl, hexyl, and isomers thereof. In one aspect of these embodiments, at least one of $R_4$, $R_5$, and $R_6$ is $C_4$ or $C_5$ alkyl, often t-butyl or t-amyl.

In one embodiment, $R_1$, $R_2$, and $R_3$ are independently selected groups of the structure:

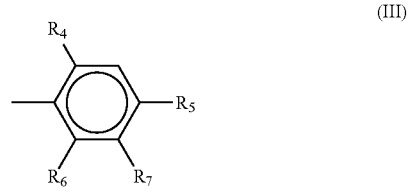

wherein $R_4$, $R_5$, and $R_6$ are defined above and $R_7$ is hydrogen or methyl, provided that one of $R_4$, $R_5$, $R_6$, and $R_7$ is methyl and that at least two of $R_4$, $R_5$, $R_6$, and $R_7$ are not hydrogen. Such phosphites are formed, for example, by the reaction of one or more alkylated cresol compounds, e.g., alkylated ortho-, meta- and/or para-cresol, with a phosphorous halide such as $PCl_3$.

The phosphite compositions typically have an overall phosphorus content that is equal to or greater than TNPP, e.g., at least 4.5 mole %, e.g., at least 4.8 mole %, or at least 5.1 mole %. In terms of ranges, the overall phosphorus content of the phosphite composition may range from 4.5 to 10.0 mole %, e.g., from 4.8 to 8.0 mole %, or 5.1 to 6.0 mole %, of all phosphorous containing compounds in the phosphite composition.

In general, the liquid phosphite composition has a low level or is substantially free of phenolics (e.g., phenols, cresols or xylenols), whether alkylated or unalkylated, referred to herein as "free phenolics" when contained in the phosphite composition. In many embodiments, a minor amount of free phenolics may be beneficial, for example, as a viscosity reducing agent. These free phenols of the invention are generally unreacted phenolics from the reaction with phosphorous trihalide and reflect the structures of the alkylated aryl groups of the phosphites, for example, the free phenols have the structures:

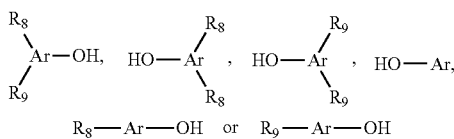

wherein $R_8$ and $R_9$ are as described above. The phosphite composition preferably comprises 0 to 10 wt % free phenols, for example, 0.01 to 5 wt %, 0.01 to 4 wt %, 0.5 to 3 wt % or 0.1 to 3 wt %, based on the combined weight of phosphites and the free shown phenols above. In one embodiment, the phosphite composition comprises a minor amount of free phenolics, e.g., from 0.1 to 5 weight percent or 1 to 5 weight percent, e.g., 0.1 to 4 weight percent, e.g., from 2 to 3 weight percent, for example, there is less than 5 wt %, e.g., less than 3 wt %, less than 1 wt %, of free phenolics, and in some embodiments less than less than 0.5 wt %, e.g., less than 0.2 wt % or less than 0.1 wt %. Phosphites are often used in combination with certain hindered phenol primary antioxidants, and the present phosphite compositions may also be used in combination with such primary antioxidants. However, the composition of the present invention is specifically a mixed phosphite composition, which is liquid at room temperature when it consists essentially of the phosphites described above and the free phenolics of the preceding structures, which composition may be blended with other materials.

In addition, the phosphite composition is often substantially free of phosphite compounds having unsubstituted aryl moieties, e.g., triphenylphosphites, bis(phenyl)alkylphenyl phosphites or bis(alkylphenyl)phenyl phosphites. That is, the phosphite composition typically comprises less than 2 wt %, e.g., less than 1 wt % or less than 0.5 wt %, phosphite compounds having an unsubstituted aryl moiety, based on the total weight of the phosphite composition. Alternatively, the alkylate used to prepare the phosphite composition may contain a minor amount of phenol, i.e., 10% or less, typically less than 5%, e.g., from 0.01 to 10 weight percent, 0.01 to 5 weight % phenol, and generally 3% or less, which may react during the phosphite synthesis process to form phenyl phosphites.

Thus, the composition of the present invention is generally a phosphite composition of at least two different alkylaryl phosphites, comprising at least a first alkylaryl phosphite and a second alkylaryl phosphite of structure (XI)

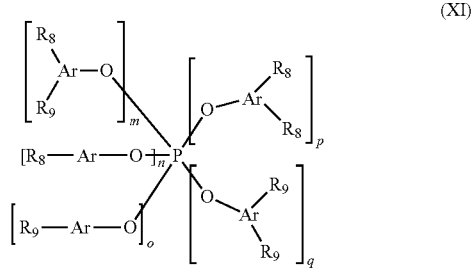

(XI)

wherein m, n, o, p and q are integers independently selected from 0, 1, 2 and 3 provided that m+n+o+p+q=3, each Ar is an independently selected aromatic moiety of 6 to 18 carbon atoms, preferably phenyl, each $R_8$ is a straight or branched $C_1$-$C_{18}$ alkyl group having the same number of carbon atoms, and each $R_9$ is a straight or branched $C_1$-$C_{18}$ alkyl group having the same number of carbon atoms, provided that $R_8$ has a different number of carbon atoms than $R_9$, said first aralkyl phosphite contains an aromatic moiety substituted by at least one $R_8$ and said second aralkyl phosphite contains an aromatic moiety substituted by at least one $R_9$, wherein the molar ratio of $R_8$ groups to $R_9$ groups in the phosphites of the composition is from 1:10 to 10:1, and from 0 to 10% by weight of one or more free phenol having the structure:

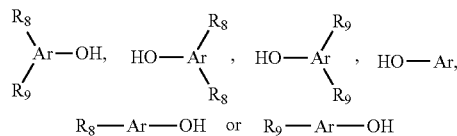

based on the combined weight of all phosphites and said free phenol in the composition, wherein the phosphite composition comprises one or more tris(monoalkylaryl)phosphites of structure (XI) wherein m, p and q are 0 and n+o=3, such as a tris(4-tert-alkylphenyl)phosphite, in an amount from 20 to 80 weight percent and one or more bis(monoalkylaryl)dialkylaryl phosphites of structure (XI) wherein m+p+q=1 and n+o=2, such as a bis(4-tert-alkylphenyl)-2,4-di-tert-alkylphenylphosphite, in an amount from 15 to 60 weight percent, based on the total weight of all phosphites in the phosphite composition, wherein the composition is a liquid at ambient conditions.

The phosphite composition also typically comprises one or more bis(dialkylaryl) monoalkylaryl phosphites of structure (XI) wherein m+p+q=2 and n+o=1 in an amount of from 2 to 20 weight percent, e.g., from 4 to 20 weight percent or from 5 to 10 weight percent, based on the total weight of all phosphites in the phosphite composition. Typically tris(dialkylaryl) phosphites of structure (XI) wherein m+p+q=3 and n and o are 0 are also present in an amount from 0.1 to 20 weight percent, e.g., from 0.3 to 5 weight percent or from 0.5 to 1 weight percent, based on the total weight of all phosphites in the phosphite composition.

The relative amounts of the phosphites in the phosphite composition may vary so long as the phosphite composition is a liquid at ambient conditions. In one embodiment, the molar ratio of the first phosphite(s) to the second phosphite(s), is from 1:10 to 10:1, e.g., from 1:4 to 4:1 or from 2:1 to 1:1. For example, by including a greater amount of phosphites with smaller alkyl groups, the overall phosphorus content may be advantageously maximized or one of the phosphites is chosen to improve, e.g., lower, the viscosity and processing characteristics for the overall phosphite composition.

In some embodiments, the phosphite composition includes one or more hydrolytic stabilizers. Preferred stabilizers include amines of the structure:

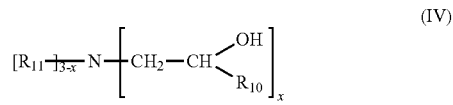

(IV)

wherein x is 1, 2 or 3; $R_{10}$ is selected from the group consisting of hydrogen, and straight or branched $C_1$-$C_6$ alkyl, preferably straight or branched $C_1$-$C_4$ alkyl, e.g., methyl or ethyl and $R_{11}$ is a straight or branched $C_1$-$C_{30}$ alkyl, preferably $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_{11}$ is straight or branched $C_5$-$C_{20}$ alkyl, e.g., $C_{12}$-$C_{18}$ alkyl. In one embodiment, x is 2 and $R_{11}$ is straight or branched $C_{10}$-$C_{20}$ alkyl, e.g., $C_{12}$-$C_{18}$ alkyl.

In one aspect the amine is selected from the group consisting of triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol) amine, octyl-bis(2-propanol)amine, nonyl-bis(2-propanol) amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof.

Additional hydrolytic stabilizers include epoxies such as epoxidized soybean oil (ESBO) commercially available as Drapex™ 39, Drapex 392, Drapex 4.4, and Drapex 6.8 (Chemtura Corp.).

The amine may be present in an amount of from 0.01 to 5 wt %, e.g., from 0.1 to 1.5 wt % or from 0.2 to 0.8 wt %, based on the total weight of the phosphite composition.

The general embodiments of the present invention are described in more detail below.

Mixed Phosphites Embodiment

In one general embodiment the phosphite compositions comprise one or more first phosphites having exclusively first alkyl groups and one or more second phosphites having exclusively second alkyl groups, wherein the first alkyl groups have a different number of carbon atoms than the second alkyl groups. The phosphite compositions comprise phosphites having at least the following two structures:

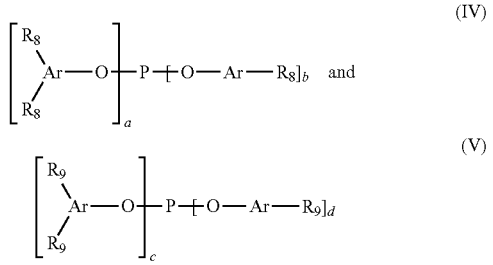

wherein a, b, c, and d are independently integers selected from 0, 1, 2, and 3, provided that a+b=3 and c+d=3, Ar, $R_8$ and $R_9$ are as described above.

For example, the first phosphite comprises aryl moieties with Alkyl-A groups, i.e., alkyl groups having A carbon atoms, and the second phosphite comprises aryl moieties with Alkyl-B groups, i.e., alkyl groups having B carbon atoms. It should be noted that each of Alkyl-A and Alkyl-B may include multiple isomers of alkyl groups having the same number of carbon atoms. For example, Alkyl-A groups may include sec-butyl and t-butyl, and Alkyl-B groups may include sec-amyl and t-amyl.

The first phosphite is therefore selected from the group consisting of tris(Alkyl-A-aryl)phosphite, tris(di-Alkyl-A-aryl)phosphite, bis(Alkyl-A-aryl)di-Alkyl-A-aryl phosphite, and bis(di-Alkyl-A-aryl)Alkyl-A-aryl phosphite; and the second phosphite is selected from the group consisting of tris (Alkyl-B-aryl)phosphite, tris(di-Alkyl-B-aryl)phosphite, bis (Alkyl-B-aryl)di-Alkyl-B-aryl phosphite, and bis(di-Alkyl-B-aryl)Alkyl-B-aryl phosphite. Other phosphites may also be present.

To elaborate, when Alkyl-A is isopropyl and Alkyl-B is t-butyl the first phosphite is selected from the group consisting of tris(4-isopropyl phenyl)phosphite, tris(2,4-dipropylphenyl)phosphite, bis(4-propylphenyl)-2,4-dipropylphenyl phosphite, and bis(2,4-di-isopropylphenyl)-4-isopropylphenyl phosphite and the second phosphite is selected from the group consisting of tris(4-t-butylphenyl)phosphite, tris(2,4-di-t-butylphenyl)phosphite, bis(4-t-butylphenyl)-2,4-di-t-butylphenyl phosphite, and bis(2,4-di-t-butylphenyl)-4-t-butylphenyl phosphite.

In another example, Alkyl-A is isopropyl and Alkyl-B is t-amyl and thus the first phosphite is selected from the group consisting of tris(4-isopropyl phenyl)phosphite, tris(2,4-di-isopropyl phenyl)phosphite, bis(4-isopropyl phenyl)-2,4-di-isopropyl phenyl phosphite, and bis(2,4-di-isopropyl phenyl)-4-isopropyl phenyl phosphite, and the second phosphite is selected from the group consisting of tris(4-t-amylphenyl) phosphite, tris(2,4-di-t-amylphenyl)phosphite, bis(4-t-amylphenyl)-2,4-di-t-amylphenyl phosphite, and bis(2,4-di-t-amylphenyl)-4-t-amylphenyl phosphite.

In a third example, Alkyl-A is t-butyl and Alkyl-B is t-amyl, so that a first phosphite is selected from the group consisting of tris(4-t-butylphenyl)phosphite, tris(2,4-di-t-butylphenyl) phosphite, bis(4-t-butylphenyl)-2,4-di-t-butylphenyl phosphite, and bis(2,4-di-t-butylphenyl)-4-t-butylphenyl phosphite and a second phosphite is selected from the group consisting of tris(4-t-amylphenyl) phosphite, tris(2,4-di-t-amylphenyl)phosphite, bis(4-t-amylphenyl)-2,4-di-t-amylphenyl phosphite, and bis(2,4-di-t-amylphenyl)-4-t-amylphenyl phosphite.

In some embodiments, the phosphite composition comprises at least three, e.g., at least four or at least five, of the generic or specific phosphites identified above.

The phosphite composition comprises tris(monoalkylaryl) phosphites, e.g., tris(Alkyl-A-phenyl) phosphite and tris (Alkyl-B-phenyl)phosphite, in an amount from 20 to 80 weight percent, in some embodiments from 55 to 80 weight percent, 20 to 55 weight percent, or from 37 to 54 weight percent, based on the total weight of all phosphites in the phosphite composition. The tris(monoalkylaryl)phosphite component may be tris(Alkyl-A-aryl)phosphite or tris(Alkyl-B-aryl) phosphite, but often, the tris(monoalkylaryl)phosphite component comprises both the tris(Alkyl-A-aryl)phosphite and tris(Alkyl-B-aryl)phosphite The phosphite composition also comprises bis(monoalkylaryl)dialkylaryl phosphites, e.g., bis(Alkyl-A-phenyl)di-Alkyl-A-phenyl phosphite, and bis(Alkyl-B-phenyl)di-Alkyl-B-phenyl phosphite, in an amount from 15 to 60 weight percent, e.g., from 31 to 50 weight percent, based on the total weight of all phosphites in the phosphite composition. As with the tris(monoalkylaryl)phosphite above, the bis (monoalkylaryl) dialkylaryl phosphite component of this general embodiment may be a combination of (Alkyl-A-aryl) di-Alkyl-A-aryl phosphite and bis(Alkyl-B-aryl)di-Alkyl-B-aryl phosphite.

If present, the phosphite composition comprises bis(dialkylaryl)monoalkylaryl phosphites, e.g., bis(di-Alkyl-A-phenyl)Alkyl-A-phenyl phosphite and bis(di-Alkyl-B-phenyl)Alkyl-B-phenyl phosphite, in an amount of from 2 to 20 weight percent, e.g., from 4 to 20 weight percent or from 5 to 10 weight percent, based on the total weight of all phosphites in the phosphite composition. If present, the phosphite composition comprises tris(dialkylaryl) phosphites, e.g., tris(di-Alkyl-A-phenyl)phosphite and/or tris(di-Alkyl-B-phenyl) phosphite in an amount from 0.1 to 20 weight percent, e.g., from 0.3 to 5 weight percent or from 0.5 to 1 weight percent, based on the total weight of all phosphites in the phosphite composition.

The phosphite compositions of the mixed phosphite embodiment are typically prepared by separately making each phosphite and blending the separate phosphites together.

The phosphites can also be conveniently prepared by reacting a phosphorous trihalide with a first alkylate composition, which may be a mixture of mono, di and optionally tri substituted aryls formed from the reaction between a hydroxyaryl compound and a first olefin, similarly reacting a phosphorous trihalide with a second alkylate composition formed from the reaction between a hydroxyaryl compound and a second olefin, wherein the second olefin has a different number of carbon atoms than the first olefin as in the scheme below.

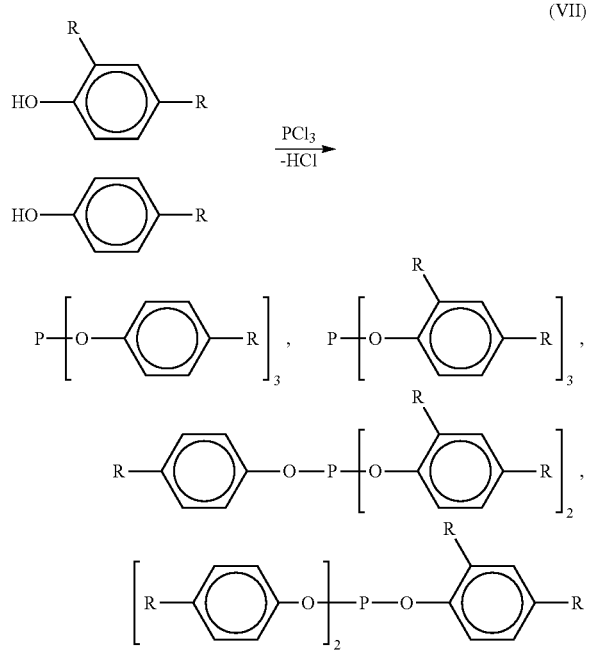

The two reaction mixtures are then combined. A minor amount of other alkylated phenols, e.g., ortho-substituted monoalkylated phenols, may be included as an additional reactant in the above reaction scheme and would form additional derivative phosphites, but these additional reactants and products have been omitted from this reaction for clarity.

As the invention comprises two different phosphites having different alkyl groups, one or more of the products shown above in scheme (VII), optionally may be separated or partially separated (e.g., through distillation) from the other reaction products. In this aspect, two relatively pure phosphites may be optionally heated and blended to form a mixture of phosphite compounds, each having a different alkyl groups.

Mixed Alkylates Embodiment

In the second general embodiment, the liquid alkylaryl phosphite compositions comprise two or more phosphite compounds, wherein at least some of the phosphite compounds are substituted with multiple alkyl groups including at least a first alkyl group and a second alkyl group having a different number of carbon atoms than the first alkyl group, provided that no individual aryl moiety is substituted with both the first alkyl group and the second alkyl group. That is, each respective aryl moiety is substituted exclusively with either the first alkyl group or the second alkyl group, but not both.

At least one of the phosphites in this embodiment therefore has the structure (VI):

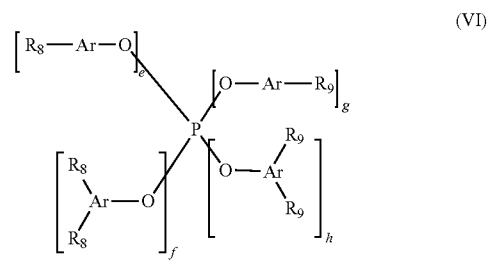

wherein e, f, g and h are independently selected from 0, 1 and 2, provided that e+f+g+h=3, e+f=1 or 2, and g+h=1 or 2, Ar, $R_8$ and $R_9$ are as described above.

In this embodiment, the phosphite composition comprises phosphites, selected from the group consisting of bis(Alkyl-A-aryl)di-Alkyl-B-aryl phosphite, bis(Alkyl-B-aryl)di-Alkyl-A-aryl phosphite, bis(di-Alkyl-A-aryl)Alkyl-B-aryl phosphite, bis(di-Alkyl-B-aryl)Alkyl-A-aryl phosphite, (Alkyl-A-aryl)(Alkyl-B-aryl)(di-Alkyl-A-aryl)phosphite, (Alkyl-A-aryl)(Alkyl-B-aryl)(di-Alkyl-B-aryl) phosphite, (Alkyl-A-aryl)(di-Alkyl-B-aryl)(di-Alkyl-A-aryl)phosphite, (Alkyl-B-aryl)(di-Alkyl-B-aryl)(di-Alkyl-A-aryl)phosphite, bis(di-Alkyl-A-aryl)di-Alkyl-B-aryl phosphite, and bis(di-Alkyl-B-aryl)di-Alkyl-A-aryl phosphite. Other phosphites, possibly having an alkyl substituents other than Alkyl-A and Alkyl-B, may also be included in the phosphite composition.

As before, the tris(monoalkylaryl)phosphite of the present compositions can include either or both of tris(Alkyl-A-aryl)phosphite and tris(Alkyl-B-aryl)phosphite, but in this embodiment, as in the mixed alkylate embodiment, the tris (monoalkylaryl)phosphites may also comprise bis(Alkyl-A-phenyl)Alkyl-B-aryl phosphite and bis(Alkyl-B-phenyl) Alkyl-A-aryl phosphite.

In particular aspects of this embodiment, Alkyl-A is propyl, e.g., isopropyl, and Alkyl-B is butyl, e.g., t-butyl; in another aspect, Alkyl-A is propyl, e.g., isopropyl, and Alkyl-B is amyl, e.g., t-amyl; in another aspect, Alkyl-A is butyl, e.g., t-butyl, and Alkyl-B is amyl, e.g., t-amyl.

In this embodiment, the phosphite compositions may be particularly diverse containing many different phosphite compounds. For example a tris(monoalkylaryl)phosphite and a tris(dialkylaryl)phosphite may include tris compounds having exclusively the same alkyl groups (either Alkyl-A or Alkyl-B), or may comprise a mixture of alkyl groups (e.g., Alkyl-A and Alkyl-B). Similarly, the bis(dialkylaryl)monoalkylaryl phosphites and bis(monoalkylaryl)dialkylaryl phosphites may include exclusively the same alkyl group or different alkyl groups.

Generally, the phosphites of the second embodiment are reaction products of a phosphorous halide and an alkylate composition that is a mixture of alkylated hydroxyaryl compounds, some of which are alkylated with Alkyl-A and some of which are alkylated with Alkyl-B. As opposed to the preparation of the mixed phosphite embodiment, the alkylated hydroxyaryl compounds are combined to form a mixed alkylate composition prior to reaction with a phosphorous halide. For example, the alkylate composition may comprise, (i) a first alkylate composition comprising mono and/or di-Alkyl-A-phenols, and (ii) a second alkylate composition comprising mono and/or di-Alkyl-B-phenols.

In one preferred embodiment, the alkylate composition comprises two or more compounds selected from the group consisting of a propylated hydroxyaryl compound, a butylated hydroxyaryl compound and an amylated hydroxyaryl compound. The propylated hydroxyaryl compound preferably is selected from the group consisting of 4-isopropyl phenol and 2,4-di-isopropyl phenol; the butylated hydroxyaryl compound preferably is selected from the group consisting of 4-t-butyl phenol and 2,4-di-t-butyl phenol; and the amylated hydroxyaryl compound preferably is selected from the group consisting of 4-t-amyl phenol and 2,4-di-t-amyl phenol, although in many embodiments other isomers and/or other alkyl groups are present.

Mixed Olefins Embodiment

In the third general embodiment of the present invention, the liquid phosphite composition comprises one or more, preferably two or more, three or more, or four or more phosphites, having at least one aryl moiety that includes two or more alkyl groups having a different number of carbon atoms, for example, the phosphite composition comprises at least one phosphite of the structure:

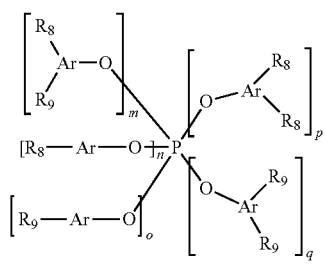

(XI)

wherein m is an integer selected from 1, 2 and 3; n, o, p and q are integers independently selected from 0, 1 and 2, provided that m+n+o+p+q=3, Ar, $R_8$ and $R_9$ are as described above. Typically, $R_8$ and $R_9$ are selected from isomers of propyl, butyl and amyl, as in the previously described general embodiments. Other phosphites may also be present including phosphites not having the general structure (XI).

In this embodiment, the phosphite compositions may be particularly diverse containing many different phosphite compounds, potentially more than in either the first or second general embodiments because each individual aryl moiety has the option of being substituted by both $R_8$ and $R_9$. That is a third alkylaryl moiety, Alkyl-A-Alkyl-B-aryl is also available.

Generally, the liquid phosphite composition of the third general embodiment is a reaction product of a phosphorous halide and an alkylate composition, where the alkylate composition is the reaction product of two or more olefins having different numbers of carbon atoms and at least one hydroxyaryl compound. Thus, while the mixed phosphites embodiment prepares Alkyl-A substituted aryl phosphites and Alkyl-B substituted aryl phosphites separately and the mixed alkylates embodiment prepares the alkylated hydroxyaryls separately but mixes them prior to reaction with phosphorous halide, the mixed olefins embodiment prepares a mixture of alkylates by reaction of an hydroxyaryl moiety with different olefins and then reaction this mixture with a phosphorous halide. Using different olefins in the process allows the formation of hydroxyaryl compounds, at least some of which are substituted with two or more alkyl groups having different numbers of carbon atoms. The composition of the alkylate composition may be modified by varying types and ratios of the reactants (e.g., olefins to hydroxyaryl compound as well as the ratio of first olefin to second olefin) and/or by modifying processing conditions of the alkylation process. The mixture of olefins independently includes two or more straight or branched $C_2$-$C_{18}$ olefins, e.g., $C_3$-$C_5$ olefins, or $C_4$-$C_5$ olefins. In one embodiment, the first olefin is a $C_2$-$C_{12}$ olefin and the second olefin is a $C_3$-$C_{18}$ olefin. Preferably, at least one of the first or second olefins is a branched olefin. Often the olefins include propylene, isobutylene and isoamylene.

During the alkylation, the mixture of olefins may be reacted in parallel with the hydroxyaryl compound, i.e., the first and second olefins are reacted together. In another embodiment, the mixture of olefins may be reacted with the hydroxyaryl compound in a consecutive manner, e.g., the first olefin is reacted first followed by the second olefin. Each of these embodiments is described in detail below.

Alkylation of Hydroxyaryl Moieties

The hydroxyaryl compound in each embodiment is an aromatic moiety having at least one hydroxyl and from 6 to 18 carbon atoms, e.g., phenol, 1-naphthol 2-naphthol, 9-phenanthrol, indanol, catechol, resorcinol, anthracen-2-ol, 4-biphenol, 4,4'-biphenol, xylenol, cresol, and derivatives thereof, preferably phenol.

In one aspect, as in the mixed phosphite and mixed alkylates embodiments, each alkyl substituted hydroxyaryl, also referred to herein as an alkylate, may be separately formed by the reaction between an olefin, e.g., propylene, butylene or amylene, and a hydroxyaryl compound, e.g., phenol. For example, the first alkylate is derived from a first olefin, and the second alkylate is derived from a second olefin having a different number of carbon atoms than the first olefin. Alternatively, as in the mixed olefins embodiment, the alkylate composition may be formed in a single reaction between the first and second olefins and the hydroxyaryl compound, for example, a mixture of alkenes such as lower alkenes (e.g., two or more $C_3$-$C_6$ olefins, such as a mixture of butylene and amylenes) may be reacted with a phenol either in parallel (feed in olefin A and B at the same time) or consecutively (i.e. olefin A is reacted first followed by olefin B).

Thus, the alkylates may be formed by contacting one or more phenolics with two or more olefins (in separate reactions or in a single reaction process) in the presence of a catalyst and under conditions effective to form the alkylate composition. Each of the two or more olefins contains from 2 to 18 carbons, e.g., from 2 to 8 carbons, or from 3 to 5 carbons, provided that the first olefin has a different number of carbon atoms than the second olefin. As an alternative to using an olefin alkylating agent, one or more $C_1$-$C_{18}$ alkyl halides, alcohols, MTBE or TAME may be employed. The alkylating agents may comprise or be derived from a hydrocarbon stream comprising alkanes and alkenes, such as a petrochemical raffinate stream from a $C_4$ or $C_5$ fraction, or a dehydrogenation reaction product of an alkane, e.g., isobutane or isopentane. In this aspect, the alkanes pass through the alkylating process unaltered and may be easily separated from the product alkylate composition.

The ratio of olefins to phenolic is such that the resulting alkylate composition is suitable for conversion to the desired phosphite composition when reacted with a phosphorous halide, keeping in mind that the resulting alkylate, e.g., first alkylate, may be blended with another alkylate, e.g., second alkylate, to form the alkylate composition that will be used in synthesizing the phosphite composition. In some exemplary embodiments, the total olefins to phenolic compound mole ratio ranges from 1:1 to 6:1, e.g., from 1.1:1 to 2:1 or from 1.25:1 to 1.4:1. The ratios may vary depending, for example, on the catalyst used in the alkylation process and the desired composition and viscosity for the ultimately formed phosphite composition.

In certain embodiments, the reaction of the phenol and the two or more olefins (whether forming the first and second alkylates separately or together) occurs in an inert atmosphere (e.g., under nitrogen) at a temperature of from 60 to 160° C., e.g., from 70 to 145° C. or from 80 to 140° C., generally at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour. The alkylation is typically performed in the presence of a catalyst. The catalyst may, for example, be selected from the group consisting of acid clay catalyst, cationic ion exchange resins, Brönsted acids, e.g., sulfuric acid, trifluoromethanesulfonic acid (triflic acid) and phosphotungstic acid, and Lewis acids, e.g., $BF_3$. Suitable commercial acid clay catalysts include Fulcat™ 22B. In one embodiment, the sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. Many common commercial cation exchange resins are useful in the present invention and include for example styrene-divinylbenzene types of strong acid ion exchange resins such as Dowex™ 50WX4, Dowex 50WX2, Dowex M-31, Dowex Monosphere M-31, Dowex DR-2030 and Dowex Monosphere DR-2030 catalysts. Other appropriate resins include: Amberlyst™ 15, Amberlyst 131, Amberlyst 35, Amberlyst 36, and A21; Diaion™ WA30, Diaion SK104, Diaion SK1B, Diaion PK208, Diaion PK212 and Diaion PK216; Tulsion™ T-38, Tulsion T-62, Tulsion T-66, Tulsion T-3825 and Tulsion T-3830; Lewatit™ K1131, Lewatit K1221, Lewatit K1261 and Lewatit SC 104; Indion™ 180 and Indion 225; and Purolite™ CT-175, Purolite™ CT-169, and Purolite™ CT-275.

In one embodiment, a batch alkylate synthesis takes place in a pot-type reactor. In another embodiment, the alkylate synthesis is conducted on a continuous basis in a continuous type reactor. In one aspect of the process, any free phenolic compounds that are not reacted with the olefins may be removed from the mixture of reaction products through distillation at a temperature, for example, of from 70 to 160° C. and at a pressure of from 1 to 10 mbar.

The components and component concentrations in the alkylate composition will vary depending on the desired composition and target viscosity for the alkylate composition as well as the ultimately formed phosphite composition. For example, in one embodiment the alkylate composition comprises 4-butyl phenol, e.g., 4-t-butyl phenol, and 2,4-diamyl phenol, e.g., 2,4-di-t-amyl phenol, in combination in an amount greater than 80 wt %, 90 wt % or greater than 95 wt %. In other specific examples, the alkylate composition comprises 4-amyl phenol, e.g., 4-t-amyl phenol, and 2,4-dibutyl phenol, e.g., 2,4-di-t-butyl phenol; 4-isopropyl phenol and 2,4-dibutyl phenol, e.g., 2,4-di-t-butyl phenol; 4-butyl phenol, e.g., 4-t-butyl phenol, and 2,4-di-isopropyl phenol; 4-isopropyl phenol and 2,4-diamyl phenol, e.g., 2,4-di-t-amyl phenol; or 4-amyl phenol, e.g., 4-t-amyl phenol, and 2,4-di-isopropyl phenol; each in combination in an amount greater than 80 wt %, 90 wt % or greater than 95 wt. %. In other embodiments, the alkylate composition comprises a complex mixture of phenolics, for example, comprising three or four of the following: a 4-butyl phenol (e.g., 4-t-butyl phenol), a 2,4-dibutyl phenol (e.g., 2,4-di-t-butyl phenol), 4-amyl phenol (e.g., 4-t-amyl phenol), and a 2,4-diamyl phenol (e.g., 2,4-di-t-amyl phenol), preferably in combination in an amount greater than 80 wt %, 90 wt % or greater than 95 wt. %. Similar complex alkylate compositions are also possible with propyl/amyl and propyl/butyl, as well as other combinations of $C_{1-18}$ alkyl groups.

In terms of component concentrations, the alkylate composition may comprise, for example, from 5 to 95 wt %, e.g., from 10 to 80 wt % or from 30 to 65 wt %, of one or more p-alkylated phenol and from 10 to 70 wt % or from 30 to 65 wt %, of one or more o,p-dialkylated phenol.

Typically, the alkylate composition comprises a monoalkyl phenol, e.g., one or more 4-alkyl phenols, and a dialkyl phenol, e.g., one or more 2,4-di-alkyl phenols. The 4-alkyl phenol is typically present in an amount greater than 40 wt %, greater than 50 wt %, greater than 60 wt %, greater than 70 wt % or greater than 75 wt % and in an amount less than 95 wt %, e.g., less than 85 wt %, less than 80 wt %, less than 75 wt % or less than 65 wt %. In terms of ranges, in some embodiments, the 4-alkyl phenol, is present in an amount ranging from 25 wt % to 99 wt %, e.g., from 45 wt % to 80 wt %, from 60 wt % to 75 wt %, or from 65 wt % to 75 wt %. In this aspect, the dialkyl phenols, typically are present in an amount ranging from 1 wt % to 60 wt %, e.g., from 10 wt % to 50 wt %, from 25 wt % to 40 wt %, or from 25 wt % to 35 wt %. Optionally, the dialkyl phenol is present in an amount less than 60 wt %, e.g., less than 55 wt %, less than 45 wt % or less than 35 wt %. In terms of lower range limitations, the dialkyl phenol, e.g., 2,4-di-t-amyl phenol and/or 2,4-di-t-butyl phenol, optionally is present in an amount greater than 10 wt %, greater than 20 wt %, greater than 30 wt %, or greater than 40 wt %.

The weight ratio of monoalkyl phenols to dialkyl phenols, is selected or adjusted so as to produce the desired alkylate composition that is suitable for being used as a reactant for forming an alkylaryl phosphite composition that is a liquid at ambient conditions. For example, the weight ratio of monoalkyl phenols to dialkyl phenols in the alkylate compositions ranges from 9:1 to 1:1, e.g., from 8:1 to 1:1, from 8:1 to 1.5:1, or from 7:1 to 2:1.

As stated above, the mixed olefins embodiment is typically formed from a mixture of alkylates prepared by reaction of an hydroxyaryl moiety with different olefins, often using either the parallel alkylation process or the consecutive alkylation process.

When fed in parallel, i.e., parallel alkylation, the alkylate composition may be formed by contacting one or more hydroxyaryl compounds with a mixture of two or more olefins, typically in the presence of a catalyst, and under conditions effective to form the alkylate composition as described in preceding embodiments. As an alternative to using an olefin alkylating agent, two or more alkyl halides or alcohols may be employed where the two or more alkyl halides or alcohols have different numbers of carbon atoms. The alkylating agent that is employed may comprise or be derived from a petrochemical raffinate stream, e.g., a $C_4$ or $C_5$ raffinate stream, comprising a combination of both alkanes and alkenes.

In one embodiment, the mixture of olefins is pre-mixed prior to the alkylation of the hydroxyaryl compound.

A schematic of one reaction method using parallel alkylation to form an alkylate composition is shown below, where $Olefin_1$ and $Olefin_2$ are independently straight or branched $C_2$-$C_8$, e.g., $C_3$-$C_5$ or $C_4$-$C_5$, olefins having a different number of carbon atoms and R is the alkyl group formed from $Olefin_1$, and R' is the alkyl group formed from $Olefin_2$.

(IX)

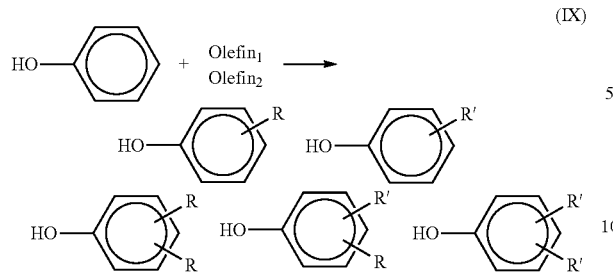

As before, the molar ratio of hydroxyaryl compound to the olefin mixture is such that the resulting alkylate composition is suitable for conversion to the desired phosphite composition when reacted with a phosphorous halide. For example, the hydroxyaryl compound to olefin mixture mole ratio ranges from 1:6 to 1:1, e.g., from 1:4 to 1:1.2 or from 1.5:1 to 1:1.5.

In consecutive alkylation, one or more hydroxyaryl compounds are reacted with one olefin, typically in the presence of a catalyst, and under conditions effective to form a partial alkylate composition. The molar ratio of hydroxyaryl compounds to the first olefin is from 6:1 to 1:2, e.g. from 5:1 to 2:3, or form 2:1 to 3:4. The partial alkylate composition is then reacted with the second olefin (having a different number of carbon atoms than the first olefin) under similar conditions to form the alkylate composition. Optionally, an additional amount of hydroxyaryl compounds may also be charged to the partial alkylate composition. The molar ratio of the partial alkylate to the second olefin is from 15:1 to 2:1, e.g., from 8:1 to 3:1 or from 6:1 to 4:1. When consecutively added, it is preferred that the olefin having a fewer number of carbon atoms is initially added followed by the other olefin. Alternatives to olefin alkylating agents described in context of parallel reactions may also be used in consecutive alkylation.

A schematic of one reaction method using consecutive alkylation to form an alkylate composition is as follows where Olefin₁, Olefin₂, R and R' are defined above. The conditions effective to form the desired alkylate composition are typically as described in preceding embodiments.

(X)

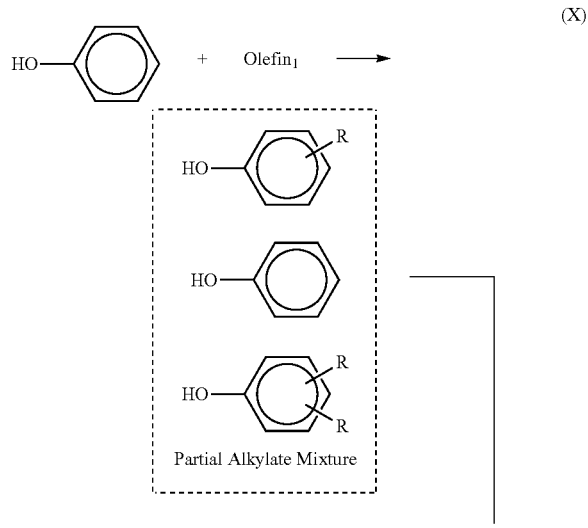

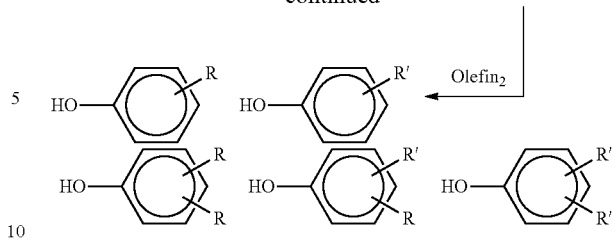

The alkylate composition thus comprises at least some dialkylated hydroxyaryl compounds, e.g., o,p-dialkylated phenols, that are substituted with both Alkyl-A and Alkyl-B. In addition, the alkylate composition may comprise a p-alkylated phenol such as p-Alkyl-A phenol, p-Alkyl-B phenol or both p-Alkyl-A phenol and p-Alkyl-B phenol. Additional o,p-dialkylated phenols in the alkylate composition may include o,p-di-Alkyl-A phenol, o,p-di-Alkyl-B phenol, or both o,p-di-Alkyl-A phenol and o,p-di-Alkyl-B phenol.

The phosphite compositions of the invention may then be conveniently prepared by reacting a phosphorous trihalide, preferably is selected from phosphorus trichloride and phosphorus tribromide with one of the above described alkylate compositions. When a catalyst is used, the catalyst may be selected from the group consisting of pyridine, N,N-dimethyldodecylamine, and dilauryl methyl amine or their hydrochloride salts. The molar ratio of alkylate composition (i.e., alkylated phenol compounds) to phosphorus trihalide preferably is from 3:1 to 5:1, e.g., from 3:1 to 4:1 or from 3.1 to 3.7:1.

The reaction of the alkylated phenols with a phosphorus trihalide may be conducted under an inert atmosphere (e.g., nitrogen) at a temperature of from 5 to 70° C., e.g., from 40 to 70° C. or from 50 to 70° C. Preferably, the temperature is held at or below 70° C. during the addition of the alkylate composition to prevent refluxing the phosphorus trihalide. Optionally, the alkylate composition is charged to the reactor and the phosphorus trihalide is added thereto. After the addition of alkylate composition, the temperature is optionally held for 10 minutes to 12 hours, e.g., from 30 minutes to 10 hours, or from 1 hour to 3 hours, typically at a pressure of 0.8 to 4 atm, e.g., from 0.9 to 3 atm or from 1 to 2 atm. Next, the temperature may be ramped to a ramped temperature ranging from 70° C. to 250° C., e.g., from 80° C. to 225° C. or from 90° C. to 200° C. Preferably, the reaction is held at the ramped temperature for from 10 minutes to 12 hours, e.g., from 30 minutes to 10 hours, or from 1 hour to 3 hours optionally at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total chloride content in the reaction mixture is less than 50 wppm, e.g., less than 25 wppm or less than 10 wppm.

In one aspect of the process, any free phenol that is not reacted with the phosphorus trihalide may be liberated by raising the reaction temperature to up to 275° C., e.g., up to 250° C. or up to 225° C., or up to 200° C., and in a vacuum at a pressure of 0.0001 to 0.1 atm. In one embodiment, a wiped-film molecular (Short-Path) still, wiped film evaporator (WFE), thin film evaporator, or similar equipment may be used to further remove the free cresol or phenol to the very low levels indicated above.

In one embodiment, the step of forming the phosphite composition occurs in one or more neutral solvents, which solvents include toluene, xylene, methylene chloride, heptane, chloroform, and benzene.

Stabilizers

A stabilizing amount or effective amount of the phosphite composition of the invention may be used as a secondary antioxidant for various types of polymers. As used herein, by "stabilizing amount" and an "effective amount" it is meant when the polymer composition containing the phosphite compositions of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to heat, light, and/or other elements. In one example, improved stability is obtained in the form of one or both of lower initial color or additional resistance to weathering, as measured, for example, by initial yellowness index (YI), or by resistance to yellowing and change in color, when compared to a composition without the stabilizer additive.

The additives and stabilizers described herein are present in an amount effective to improve composition stability. For example, the phosphite composition is generally present in an amount from about 0.001 to about 5 wt. %, e.g., from about 0.0025 to about 2 wt. % or from about 0.005 to about 1 wt. %, based on the total weight of the polymer including the weight of the phosphite composition and any other stabilizers or additives. The phosphite compositions of this invention stabilize resins especially during high temperature processing with relatively little change in melt index and/or color, even after multiple extrusions.

The invention further relates to a stabilized thermoplastics, comprising a base polymer the phosphite compositions of the invention. The polymer resin may be a polymer such as a polyolefin, and the liquid phosphite composition may be used with a costabilizer, for example, hindered phenolics, aromatic amines, hydroxylamines, lactones, and thioethers. The thermoplastic is stabilized by the phosphite compositions of the present invention optionally contains one or more additional stabilizers or mixtures of stabilizers selected from the group consisting of phenolic antioxidants, hindered amine light stabilizers (HALS), ultraviolet light absorbers, phosphites, phosphonites, alkaline metal salts of fatty acids, hydrotalcites, metal oxides, epoxydized soybean oils, hydroxylamines, tertiary amine oxides, lactones, thermal reaction products of tertiary amine oxides, and thiosynergists.

In one embodiment, the amount of each component in the stabilizing mixture, based on the total weight percent of the polymer or polymeric resin, is shown in Table 4.

TABLE 4

| Component | Range | Preferred Range |
|---|---|---|
| Liquid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating or clarifying agents | 0-3.0 wt % | 0.001-2.0 wt % |
| Aminoxy propanoate | 0-3.0 wt % | 0.001-2.0 wt % |

Primary antioxidants include the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6,-tricyclohexyphenol, and 2,6-di-tert-butyl-4-methoxymethylphenol (ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4-octadecyloxyphenol.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methyphenol).

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl)terephthalate (v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl, phosphonate, calcium salt of monoethyl 3,5-di-tert-butyl-4-hydroxybenzylphosphonate, 1,3,5-tris-(3,5-dicyclohexyl-4-hydroxybenzyl)isocyanurate.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis[methylene {3,5-di-tert-butyl-4-hydroxycinnamate}] methane.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine.

(x) Other phenolic antioxidants include polymeric phenols such as the reaction product of 4-methylphenol with dicyclopentadiene and isobutylene, alkylidene-poly-phenols, such as 1,3 tris(3-methyl-4-hydroxyl-5-t-butyl-phenyl)-butane; thio phenols such as 2,6-di-tert-butyl-4-(4,6-bis(octylthio)-1,3,5-triazin-2-ylamino)phenol, 4,6-bis(octylthiomethyl)-o-cresol; 4,6-bis(dodecylthiomethyl)-o-cresol, ester phenols include bis[3,3-bis(4-hydroxy-3-tert-butyl phenyl)butanoic acid]glycol ester and 2-[1-(2-hydroxy-3,5-di-tert-pentylphenyl)ethyl]-4,6-di-tert-pentylphenyl acrylate.

(xi) Other primary antioxidants include hydroxylamines, and n-oxides such as bis(octadecyl)hydroxylamine.

In one embodiment, the stabilizing composition comprises one primary antioxidant selected from the group consisting of tetrakismethylene (3,5-di-t-butyl-4-hydroxyhydrocinnamate) methane, 1,3,5-tris(3,5-di-t-butyl-4-hydroxybenzyl) isocyanurate, 1,3,5-tris(4-tert.-butyl-3-hydroxy-2,6-dimethylbenzyl)-1,3,5-triazine-2,4,6-(1H,3H,5H)-trione, octyl-3-(3,5-di-t-butyl-4-hydroxyphenyl)propionate, bis(octadecyl) hydroxylamine, 1,3,5-trimethyl-2,4,6-tris(3,5-di-tert-4-hydroxybenzyl)benzene, 2,6-bis(α-methylbenzyl)-4-methylphenol, 3,5-bis(1,1-dimethylethyl)-4-hydroxy-benzenepropanoic acid, 2,6-di-t-butyl-4-ethyl-phenol, and mixtures thereof, and the liquid phosphite composition defined herein.

The phosphite compositions and/or the resulting stabilized polymeric compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5' methyl-, 3'-sec-butyl-5' tert-butyl-,4'-octoxy, 3',5'-ditert-amyl-3',5'-bis-(α,α-dimethylbenzyl)-derivatives.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

(vi) Sterically hindered amines may be used as light stabilizers, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6-pentamethylpiperidyl) ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylenediamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5' di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2' ethyl-5,4-di-tert-butyloxanilide and mixtures of o- and p-methoxy—as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iii) Polyamide stabilizers, for example copper salts in combination with iodides and/or phosphorus compounds and salts of divalent manganese may also be included in the polymer resin and/or phosphite composition.

(iv) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate.

(v) Nucleating and clarifying agents, for example, metal salts of 4-tert butylbenzoic acid, adipic acid, diphenylacetic acid, sorbitol and derivatives thereof, sodium benzoate, and benzoic acid.

(vi) Aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3 (N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(vii) Other additives, for example, plasticizers, lubricants, emulsifiers, pigments, dyes, optical brighteners, flameproofing agents, anti-static agents, blowing agents and thiosynergists such as dilaurythiodipropionate or distearylthiodipropionate.

Optionally the polymer or polymeric resins may include from 5-50 wt %, e.g., 10-40 wt % or 15-30 wt % fillers and reinforcing agents, for example, calcium carbonate, silicates, glass fibers, asbestos, talc, kaolin, mica, barium sulfate, metal oxides and hydroxides, carbon black and graphite.

The invention further pertains to a stabilized polymer, wherein one component comprises a liquid phosphite composition of the present invention and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite compositions of the present invention are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite compositions are used in polymers, such as polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

The polymer may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite compositions of the present invention. These include polymers such as polychloroprene, epichlorohydrin homo and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymer, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2-(2,2,4(4-hydroxyphenyl)-propane) terephthalate and polyhydroxybenzoates as well as block copolyetheresters derived from polyethers having' hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

The phosphite compositions of the invention may have uses in addition to polymer stabilization. For example, it may be desirable to react the phosphite composition to form a new derivative product, that may of additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

The present invention is further described by way of the following non-limiting examples.

EXAMPLES

Example 1

Synthesis of Mixed Amyl/Butyl Phenols

Phenol (105 grams, 1.12 moles) and Fulcat 22B catalyst (2.25 grams) were charged to an oil jacketed flask and heated to 130° C. under nitrogen. Isobutylene (64.6 grams, 1.15 moles) was added via a sintered glass frit below the surface of the phenol at a uniform rate over 30 minutes. During addition, the internal temperature rose to 140° C. Once the addition was completed, the reaction mass was held at a jacket temperature of 130° C. for one hour. Amylene (39.2 grams, 0.56 mole) was then added below the surface of the phenolics at a uniform rate over 1.25 hours. After the addition, the reaction mass was held at a jacket temperature of 130° C. for two hours. The reaction was then filtered and the phenolic filtrate collected. The mixed butylated/amylated phenol alkylate was subjected to vacuum distillation to reduce the phenol content to less than 0.25% and the water content to less than 50 ppm. Yield=161.8 grams.

GC analysis identified the following major components: 50.8% 4-t-butyl-phenol, 17.6% 2,4-di-t-butyl-phenol, 15.3% 4-t-amyl-phenol, 10.7% 2-t-amyl-4-t-butyl-phenol and 2-t-butyl-4-t-amyl-phenol, 1.3% 2,4-di-t-amyl-phenol, 1.4% 2-t-butyl-phenol, and 0.3% 2,4,6-tri-t-butyl-phenol.

Example 2

Conversion to a Phosphite of the Alkylate Obtained as per Example 1

Mixed butylated/amylated phenolic alkylate (148.7 grams, 0.86 mole) was charged to an oil jacketed flask and heated to 80° C. under nitrogen. $PCl_3$ (35.8 grams, 0.26 mole) was added, below the surface of the phenolics, at a uniform rate over three hours. During the addition, the temperature was ramped to 150° C. The reaction mass was held at 150° C. until HCl evolution ceased, and then was heated to 200° C. over one hour while the pressure was reduced from 1000 to 50 mbar. The reaction was held at 200° C./50 mbar until the total Cl content was less than 50 ppm. The phenolic excess was then removed by distillation under one mbar pressure and an internal temperature of 240° C. (vapor temperature 140° C.). Yield=123.1 grams.

The phosphite composition had kinematic viscosity of @ 30° C. of 8,541 cSt, @ 40° C. of 3,198 cSt, and @ 50° C. of 812 cSt.

Example 3

73.4 g (0.53 moles) of phosphorous trichloride and 1.74 ml (6.41 mmols) of N,N-dimethyldodecylamine are charged to a jacketed vessel under nitrogen. The contents of the vessel are agitated and heated to 70° C. Separately, a powdered blend of 193.1 g (1.18 moles) of 4-tert-amylphenol and 121.3 g (0.56 moles) of 2,4-di-tert-butylphenol is prepared. The powdered blend is added in uniform shots of 26.2 g, every 15 minutes over 3 hours. During the addition the reaction is held at 70° C. and evolved HCl is absorbed by a scrubber unit.

Once all the phenols are added, the reaction temperature is uniformly ramped from 70° C. to 150° C. over 1 hour. The reaction mass is held at 150° C. for 1 hour or until the HCl evolution has stopped. Next, the reaction mass is further heated from 150° C. to 200° C. and held for 1 additional hour. Once the reaction mass has reached 200° C., the reaction is degassed by applying a vacuum at a pressure from 60-80 mbar until the total chlorine content is less than 50 ppm. Excess phenols may be removed by distillation under a pressure of 7 mbar up to an internal temperature of 200° C. (maximum vapor temperature 127° C.).

1.89 g (9.9 mmoles) of triisopropanolamine is added to the phosphite composition.

The resulting composition of phosphites had a kinematic viscosity at 70° C. of 97 cSt. The total phosphorous content is 5.6%.

Example 4

A 1:1 molar ratio of 2-t-butyl-p-cresol and 4-t-amylphenol were charged to an oil jacketed flask and heated to 80° C. under nitrogen. $PCl_3$ (73.4 grams, 0.53 mole) was added, below the surface of the phenolics, at a uniform rate over 2 hours. During the addition the temperature was ramped to 150° C. and the reaction mass was held at 150° C. until HCl evolution ceased. Next the reaction mass was heated to over 200° C. over 1 hour while the pressure was reduced from 1000 to 70 mbar, and held at these conditions until the total Cl content was less than 50 ppm. The phenolic excess was then removed by distillation under 8 mbar pressure and an internal temperature of 200° C. The resulting composition of phosphites had a kinematic viscosity at 70° C. of 160 cSt. The total phosphorous content is 5.9%.

Example 5

The composition of phosphites from Examples 3 and 4 were tested and compared against a tris(nonylphenyl)phosphite, Weston 399, and showed the following results in Table 3. The phosphite were added at the same phosphorous content for comparison (@ 17 ppm).

TABLE 3

| Composition | Example 3 | Example 4 | Weston 399 |
|---|---|---|---|
| LLDPE | 99.93 wt % | 99.901 wt % | 99.89 wt % |
| ZnSt | 0.05 wt % | 0.05 wt % | 0.05 wt % |
| Anox PP18 | 0.02 wt % | 0.02 wt % | 0.02 wt % |
| Phosphite Amount | 0.0305 wt % | 0.029 wt % | 0.04 wt % |
| YI (ASTM E313) during multipass @ 230° C. | | | |
| Initial | −1.284 | −1.07 | −1.249 |
| Pass 1 | 0.441 | 0.573 | 0.06 |
| Pass 3 | 0.705 | 0.952 | 0.718 |
| Pass 5 | 0.937 | 1.689 | 1.203 |
| MFI @2.16 kg during multipass @ 230° C. | | | |
| Initial | 0.975 | 0.958 | 0.967 |
| Pass 1 | 0.939 | 0.909 | 0.904 |
| Pass 3 | 0.782 | 0.781 | 0.778 |
| Pass 5 | 0.591 | 0.629 | 0.637 |
| MFI @ 21.6 kg during multipass @ 230° C. | | | |
| Initial | 23.635 | 22.817 | 23.027 |
| Pass 1 | 23.203 | 22.986 | 23.066 |
| Pass 3 | 22.022 | 21.656 | 21.614 |
| Pass 5 | 21.344 | 20.694 | 20.973 |
| MFI ratio during multipass @ 230° C. | | | |
| Initial | 24.229 | 23.814 | 23.819 |
| Pass 1 | 24.698 | 25.298 | 25.519 |
| Pass 3 | 28.149 | 27.741 | 27.765 |
| Pass 5 | 36.113 | 32.894 | 32.940 |
| YI, after NOx exposure | | | |
| 2 hours | 2.37 | 2.84 | 3.26 |
| 25 hours | 5.48 | 8.33 | 6.27 |
| 94 hours | 8.63 | 9.14 | 9.34 |
| 120 hours | 9.41 | 9.94 | 10.11 |
| 140 hours | 10.19 | — | 10.52 |

Examples 6

Using the method of Example 3, a phosphite composition was prepared from a 1:1 (molar) mixture of 4-t-amylphenol (4-TAP) and 2,4-di-t-butylphenol (2,4-DTBP). Viscosities are provided in Table 4, below.

Comparative Example A

Reaction of phosphorus trichloride (⅓ mole) with 2,4-ditertiary amyl phenol (⅔ mole) then with 2,4-ditertiary butyl phenol (⅓ mole) from U.S. Pat. No. 5,254,709 produces a solid phosphite composition.

One-third of a mole of phosphorus trichloride (46 g) was charged into a 500 ml 3-neck flask. One hundred cubic centimeters of toluene and 0.2 g mercaptobenzothiazole were added. Then 156 g (⅔ mole) of melted 2,4-di-tertiary amyl phenol was dropped in over a period of two hours, the temperature being maintained between 55° and 65° C. The temperature was then increased to 120°-123° C. for two hours. Nitrogen gas was passed through the hot mix to remove residual hydrogen chloride. The mix stood over the weekend at room temperature. An infrared analysis showed no hydroxyl. The mixture was warmed to 60° C. and 68.3 g (⅓ mole) of solid 2,4-di-tertiary butyl phenol was added. The mix was gradually heated to 127° C. (over two hours) and then heated near that temperature for three hours longer. Nitrogen gas was bubbled through the hot mix to remove residual hydrogen chloride. The toluene was removed by heating under diminished pressure. The residual product was a clear liquid that hardened to a clear glassy product on cooling. Three hundred cc of methanol was added and the mixture was stirred and heated to 60° C. The product gradually crystallized to a white powder. After standing in the methanol at room temperature overnight the solid product was filtered off and washed with 100 cc of methanol. The dried produce weighed 197.6 g (90% of theory). The material melted at 89°-93° C.

Comparative Examples B and C

Comparative Examples B and C were prepared in a similar amount with different molar ratios of phenols and different phenols as shown in Table 4 below. Comparative Examples B and C use 4-t-butylphenol (4-TBP).

TABLE 4

| Ex. | Phenol 1 | Mol | Phenol 2 | Mol | Ratio | Viscosities (cSt) @ 40° C. | @ 50° C. | @ 60° C. |
|---|---|---|---|---|---|---|---|---|
| 3 | 2,4-DTBP | 0.293 | 4-TAP | 0.588 | 1:2 | 1189 | 420 | 175 |
| 6 | 2,4-DTBP | 0.288 | 4-TAP | 0.288 | 1:1 | 32,228 | 7351 | 1810 |
| B | 2,4-DTBP | 0.661 | 4-TBP | 0.661 | 1:1 | — | 10,265 | 1678 |
| C | 2,4-DTBP | 2.938 | 4-TBP | 5.878 | 1:2 | 10,486 | 1853 | — |

As shown in Table 4, replacing 4-TBP with 4-TAP reduces the viscosity at lower temperatures, 30-50° C. In addition, providing a molar ratio of 2,4-DTBP to 4-TAP of 1:2 further reduces the viscosity.

In view of the many changes and modifications that can be made without departing from principles underlying the invention, reference should be made to the appended claims for an understanding of the scope of the protection to be afforded the invention.

What is claimed is:

1. A composition comprising a mixture of alkylaryl phosphites and from 0 to 10% by weight of one or more free phenol based on the combined weight of all phosphites and said free phenol in the composition,
said mixture of alkylaryl phosphites comprising;
one or more phosphites of structure

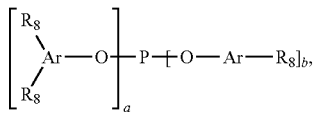

one or more phosphites of structure

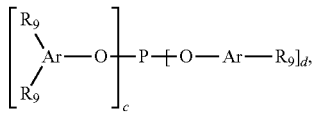

and one or more phosphites of structure

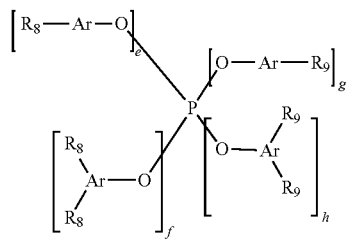

wherein
a, b, c, and d are independently selected from 0, 1, 2, and 3, provided that a+b=3 and c+d=3,
e, f, g and h are independently selected from 0, 1 and 2, provided that e+f+g+h=3, e+f=1 or 2, and g+h=1 or 2,
each Ar is phenyl,
each $R_8$ is a straight or branched $C_1$-$C_{18}$ alkyl group having the same number of carbon atoms,
each $R_9$ is a straight or branched $C_1$-$C_{18}$ alkyl group having the same number of carbon atoms, provided that $R_8$ has a different number of carbon atoms than $R_9$, and the molar ratio of $R_8$ groups to $R_9$ groups in the phosphite mixture is from 1:10 to 10:1,
which mixture of alkylaryl phosphites comprises
one or more tris(monoalkylaryl) phosphites in an amount from 20 to 80 weight percent
one or more bis(monoalkylaryl)dialkylaryl phosphites in an amount from 15 to 60 weight percent,
one or more bis(dialkylaryl)alkylaryl phosphites in an amount from 2 to 20 weight percent,
one or more tris(dialkylaryl) phosphites in an amount from 0.1 to 20 weight percent based on the total weight of all phosphites in the phosphite composition,
and said one or more free phenol is selected from the group consisting of

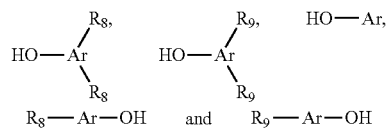

wherein $R_8$ and $R_9$ are as defined above,
wherein the composition consisting of the mixture of alkylaryl phosphites and free phenol is a liquid at ambient conditions.

2. The composition of claim 1, wherein $R_8$ and $R_9$ are selected from n-butyl, sec-butyl, t-butyl, n-amyl, sec-amyl, neo-amyl and t-amyl.

3. The composition of claim 2, wherein $R_8$ is t-butyl and $R_9$ is t-amyl.

4. The composition of claim 3, comprising from 0.01 to 5 weight percent of said free phenol.

5. The composition of claim 3, comprising less than 1 weight percent of said free phenol.

6. The composition of claim 1, comprising from 0.01 to 5 weight percent of said free phenol.

7. The composition of claim 1, comprising less than 1 weight percent of said free phenol.

8. The composition of claim 1, wherein said mixture of alkylaryl phosphites comprises
one or more tris(monoalkylaryl) phosphites in an amount from 37 to 54 weight percent
one or more bis(monoalkylaryl)dialkylaryl phosphites in an amount from 31 to 50 weight percent,
one or more bis(dialkylaryl)alkylaryl phosphites in an amount from 5 to 10 weight percent,
one or more tris(dialkylaryl) phosphites in an amount from 0.3 to 5 weight percent based on the total weight of all phosphites in the phosphite composition.

9. The composition of claim 8, wherein $R_8$ and $R_9$ are selected from n-butyl, sec-butyl, t-butyl, n-amyl, sec-amyl, neo-amyl and t-amyl.

10. The composition of claim 9, wherein $R_8$ is t-butyl and $R_9$ is t-amyl.

11. The composition of claim 10, comprising from 0.01 to 5 weight percent of said free phenol.

12. The composition of claim 10, comprising less than 1 weight percent of said free phenol.

13. The composition of claim 8, comprising from 0.01 to 5 weight percent of said free phenol.

14. The composition of claim 8, comprising less than 1 weight percent of said free phenol.

15. A stabilized polymer composition comprising a polymer and the phosphite composition of claim 1.

16. The stabilized polymer composition according to claim 15 wherein the polymer comprises a polyolefin, polyalkylene terephthalate, polyphenylene ether, styrenic polymer, polycarbonate or ABS.

17. The stabilized polymer composition according to claim 16 wherein the polymer comprises a polyethylene, polypropylene, polyethylene terephthalate, polyphenylene ether or high impact polystyrene.

18. The stabilized polymer composition according to claim 17 wherein the polymer comprises a high density polyethylene, low density polyethylene or linear low density polyethylene.

\* \* \* \* \*